United States Patent [19]

Shibata et al.

[11] Patent Number: 5,322,963

[45] Date of Patent: Jun. 21, 1994

[54] METHOD FOR PREPARING α-AMINO-β, δ-DIOL DERIVATIVES

[75] Inventors: Saizo Shibata; Eiji Shirakawa; Yasuki Yamada; Koji Ando; Itsuo Uchida, all of Yokohama, Japan

[73] Assignee: Japan Tobacco, Inc., Tokyo, Japan

[21] Appl. No.: 938,257

[22] PCT Filed: Feb. 4, 1992

[86] PCT No.: PCT/JP92/00106

§ 371 Date: Oct. 5, 1992

§ 102(e) Date: Oct. 5, 1992

[87] PCT Pub. No.: WO92/13827

PCT Pub. Date: Aug. 20, 1992

[30] Foreign Application Priority Data

Feb. 5, 1991 [JP] Japan ................................ 3-100562
Jan. 8, 1992 [JP] Japan ................................ 4-38862

[51] Int. Cl.[5] .................. C07C 213/00; C07C 215/20
[52] U.S. Cl. .................... 564/343; 560/29; 560/115; 564/92; 564/93; 564/210; 564/213; 564/342; 564/360; 564/391
[58] Field of Search ................. 564/92, 93, 210, 213, 564/342, 343, 360, 391; 560/29, 115

[56] References Cited

FOREIGN PATENT DOCUMENTS 0077099 6/1982 European Pat. Off. .
58-74644 5/1983 Japan .
3204860 9/1991 Japan .

OTHER PUBLICATIONS

An Expeditious Synthesis of (3S,4S)-Statine and (3S-4S)-Statine and (3S,4S)-Cyclohexylstatine, Tetrahedron Letters, vol. 31, No. 2, pp. 217-218, 1990.
Angew. Chem. Int. Ed. Engl 26, pp. 1141-1143, 1987.
J. Am. Chem. Soc. 1988, 110, pp. 3560-3578.

Primary Examiner—Richard L. Raymond

Attorney, Agent, or Firm—Birch, Stewart, Kolasch & Birch

[57] ABSTRACT

Intermediate compounds (formula [III] and [IV]) useful as starting materials for the synthesis of amino acid derivatives which have renin inhibitory activity and which are useful as remedies for hypertension are prepared stereoselectively in high yield, without requiring complicated process steps. In this method, by reaction of α-amino aldehyde derivative [I] and compound [II] in the presence of $BF_3 \cdot OEt_2$, as shown in the following reaction formula, α-amino-β-hydroxy-δ-ketone derivative [III] is prepared, and furthermore, by reducing it as required, compound [IV] is obtained:

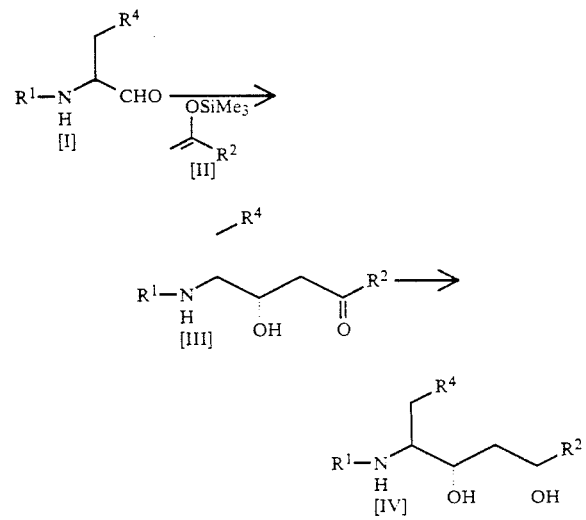

(where $R^1$ is a protective group on the amino group, $R^2$ is a lower alkyl group which may be branched, and $R^4$ is a cyclohexyl group or phenyl group).

13 Claims, No Drawings

METHOD FOR PREPARING α-AMINO-β, δ-DIOL DERIVATIVES

TECHNICAL FIELD

The present invention relates to a novel method for preparing compounds represented by the formulas [III], [IV].

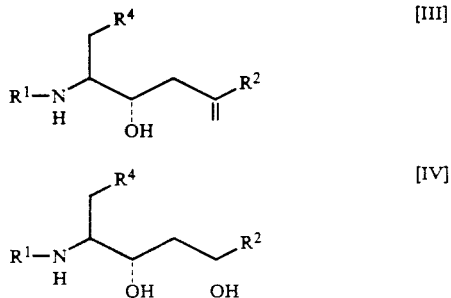

(where $R^1$ is a protective group on the amino group, $R^4$ is a cyclohexyl group or a phenyl group, and $R^2$ is a lower alkyl group which may be branched). The compounds are useful as starting materials for preparing desired compounds which have human renin inhibiting activity and are useful as hypertension remedies, examples of the desired compounds being amino acid derivatives (see EP 0396065A1) represented by following formulas [I] and [II]. More particularly, the compounds [III] and [IV] are useful as starting material for the synthesis of the A4 parts of the desired compounds [I] and [II].

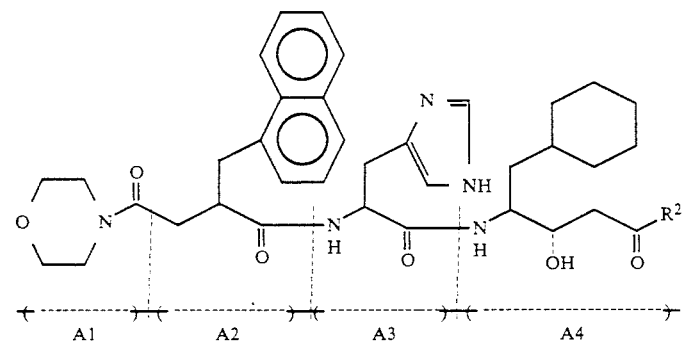

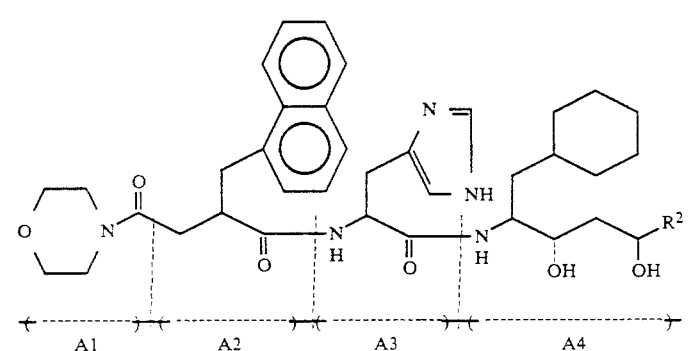

(where $R^2$ is a lower alkyl group which may be branched)

BACKGROUND ART

Both the α-amino-β-hydroxy-δ-ketone derivative (hereinafter called amino hydroxy ketone derivative) represented by formula [III] and the αamino-β, δ-diol derivative (hereinafter called amino diol derivative) represented by formula [IV] are known, and the amino diol derivative [IV] is prepared by reducing the amino hydroxy ketone derivative [III].

As the method for preparing the amino hydroxy ketone derivative [III], for example, the following methods are known.

① A method wherein α-amino aldehyde derivative [V] is reacted and condensed with a ketone derivative such as isopropyl methyl ketone, in the presence of a base such as lithium diisopropyl amide (EP 0396065A1).

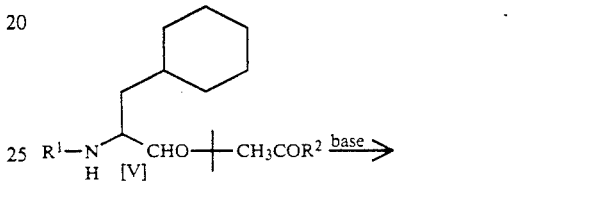

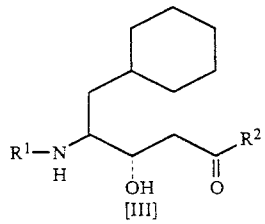

② A method wherein oxazolidine derivative [VI] having a dithiohetero cyclic group is converted to a corresponding amino hydroxy ketone [III] (EP 0396065A1), by turning the dithiohetero part of the starting derivative [VI] into an oxo form, and opening the oxazolidine ring.

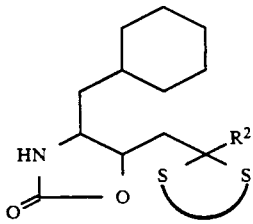

[VI]

③ A method wherein lactam derivative [VII] having the amino group protected with a tert-butoxycarbonyl group is reacted with Glignard's reagent to open the lactam ring, thereby synthesizing amino hydroxy ketone derivative III] (W090/07521).

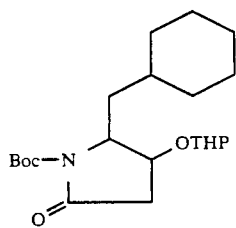

[VII]

(where THP denotes a tetrahydropyranyl group)

However, the amino hydroxy ketone derivative [III] has the configuration about the hydroxyl group in type (a) shown below, and there is a stereoisomer (b) with respect to the hydroxyl group.

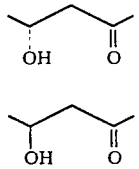

(a)

(b)

The conventional method ① does not satisfy the stereoselectivity about the hydroxyl group. The method ② is large in the number of steps, including introduction of the dithio hetero ring group and opening of the oxazolidine ring, and is complicated so that the method is not practicable. The method ③ is also complicated for practical use, requiring many steps in preparing the lactam derivative which is the starting compound.

On the other hand, there is also known a method for preparing amino diol derivative [IV] by reducing the amino hydroxy ketone derivative [III] (EP0396065A1, W090/07521). However, the configuration of this amino diol derivative [IV] is of the following type (A), while there are also three other types (B), (C), (D) of configuration about the hydroxyl group, and therefore, it is extremely difficult to selectively prepare the derivative of (A) having the desired configuration.

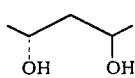

(A)

-continued

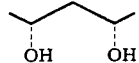

(B)

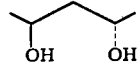

(C)

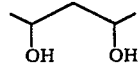

(D)

In addition, the reduction reaction of α-hydroxy-δ-ketone derivative using tetramethyl ammonium borohydride is generally lowered in stereoselectivity at high temperature, and tends to be worse in the yield of the desired compound. Conventionally, acetic acid, acetonitrile/acetic acid and the like were used as a solvent, but acetic acid freezes at 16° C. or less, and acetonitrile/acetic acid is not sufficient in the stereoselectivity although it is satisfactory in reaction at 16° C. or less.

On the other hand, a method is also known for preparing α-amino aldehyde derivative [V] which is used as starting material in the present invention (Unexamined Japanese Patent Publication 2-60595). In this method, 2-amino-1-cyclohexyl propanol is oxidized in a solvent to obtain an α-amino aldehyde derivative, and the reaction mixture is then extracted with diethyl ether, washed with water, concentrated in vacuo, and purified by silica gel chromatography. This method is, however, far from practicable not only because it is complicated in process, requiring the steps of concentration under reduced pressure and purification by chromatography, but also because racemization is induced in the process.

DISCLOSURE OF THE INVENTION

It has been discovered that the desired amino diol derivative [IV] can be manufactured in high yield, thereby completing the present invention.

The present invention is described in detail below.

The amino hydroxy ketone derivative represented by formula [III] and the amino diol derivative represented by formula [IV] may be prepared in the following reaction processes.

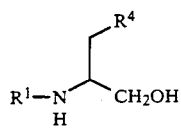

[VIII]

Step 1

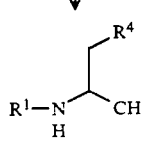

[V]

Step 2

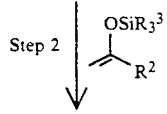

[IX]

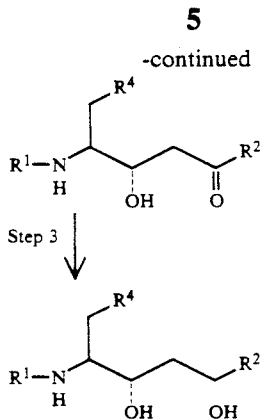

Herein, $R^1$ is a protective group for the amino acid, which may be any protective group so far as capable of protecting the amino group from various reactions. Examples include, among other, a substituted or non-substituted lower alkanoyl group such as a formyl group, acetyl group, propionyl group or trifluoroacetyl group; a lower alkoxycarbonyl group such as a tert-butoxy carbonyl group (Boc) and tert-amyloxy carbonyl group; a substituted or non-substituted aryloxy carbonyl group such as a benzyloxy carbonyl group (Z) and p-nitrobenzyloxy carbonyl group; a substituted or non-substituted aryl sulfonyl group such as a tosyl group; and an aralkyl group such as a trityl group and benzyl group. $R^2$ and $R^3$ are lower alkyl groups which may be branched, for example, a methyl group, ethyl group, n-propyl group, isopropyl group, n-butyl group, isobutyl group, sec-butyl group, tert-butyl group, n-pentyl group, 1-methyl butyl group, 2,2-dimethyl butyl group, n-hexyl group, 2-methylpentyl group, or 2,2-dimethylpropyl group. What is particularly preferable for $R^3$ is a methyl group, ethyl group, propyl group, isopropyl group, n-butyl group, isobutyl group, sec-butyl group, tert-butyl group, or the like. $R^4$ is a cyclohexyl group or phenyl group.

The above mentioned steps 1, 2, 3 are further described below.

STEP 1

This is a step for oxidizing an α-amino alcohol derivative represented by formula [VIII] to obtain an α-amino aldehyde derivative represented by formula [V]. The α-amino alcohol derivative [VIII] wherein $R^4$ is a cyclohexyl group or phenyl group is itself known, and it is easy to prepare by a known method using phenylalanine as starting material. The oxidation reaction may conform to a known method (for example, Unexamined Japanese Patent Publication 2-60595) In extraction of α-amino aldehyde derivative [V], an organic solvent such as dichloromethane or diethyl ether and the like may be used, but dichloromethane is particularly preferable. When using dichloromethane, without requiring the steps of concentration under reduced pressure of purification by silica gel chromatography in the prior art, α-amino aldehyde derivative [V] may be used in the next step directly in the form of a dichloromethane solution. Therefore, in this case, while preventing racemization due to the steps of concentration under reduced pressure and purification in the prior art, the α-amino aldehyde derivative [V] having a desired configuration may be supplied to the next step efficiently. Furthermore, by using a weak alkaline aqueous solution (preferably, for example, sodium hydrogencarbonate solution) or a weak acidic aqueous solution (preferably, for example, 0.5M citric acid solution) in the cleaning step, and using magnesium sulfate, calcium sulfate or other desiccant in the drying step, racemization may be further prevented. Or, optionally as required, by using florisil, the solution of aldehyde derivative [V] may be filtered to refine aldehyde derivative [V], and racemization may be prevented in this refining method.

STEP 2

This step is to obtain a hydroxy ketone derivative represented by formula [III] by reacting the α-amino aldehyde derivative shown in formula [V] with the silyl enol ether derivative shown in formula [IX], under in the presence of boron trifluoride ether complex or tin tetrachloride as catalyst. In particular, when the boron trifluoride ether complex is used, side reactions hardly take place as compared with the case of using other Lewis acids, and the yield is also better. This reaction is carried out in a solvent. As the solvent, any solvent not participating in the reaction may be used, and preferably dichloromethane, chloroform, carbon tetrachloride, toluene, and other non-protonic solvents may be used. The reaction temperature is not more than room temperature, and preferably −80° C. to 0° C. This reaction has a high stereoselectivity, and the compounds

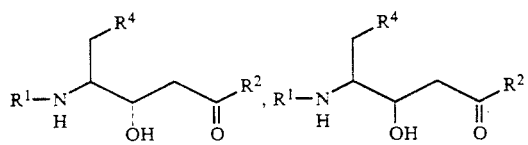

are obtained in a high ratio of 9:1. It should be noted that the boron trifluoride ether complex is a complex between boron trifluoride ($BF_3$) and ether. As a preferable ether, in this case, diethyl ether and di-n-butyl ether are particularly recommended, but these are not limitative.

STEP 3

This is a step of obtaining the amino diol derivative represented by formula [IV] by reducing the hydroxy ketone derivative shown in formula [III] stereoselectively, using tetramethyl ammonium borohydride. This reaction is a stereoselective reduction (J.A.C.S. 110, 3560-3578, 1988) by the action of a reaction intermediate between a lower alkyl carboxylic acid used as solvent and tetramethyl ammonium borohydride, that is, $Me_4NHB$ $(OOC-R^5)_3$ ($R^5$ denotes a lower alkyl group which may be branched). The lower alkyl carboxylic acid to be used as solvent is preferably propionic acid. This reaction is low in stereoselectivity and poor in the yield of the desired compound at high temperature, and the reaction temperature should be lower than room temperature, or preferably 5° C. or less, or more preferably −10° C. to 0° C. It should be noted that amino hydroxy ketone derivative [III] obtained in step 2 wherein $R^4$ is a phenyl group, and amino diol derivative [IV] obtained in step 3 wherein $R^4$ is a phenyl group are themselves usable as A4 part of renin inhibitory compounds [I], [II] as the mentioned above. In addition, these derivatives [III] and [IV] may be usable as constituent materials of the A4 part in which $R^4$ is a cyclohexyl group, when each $R^4$ of the derivatives [III] and [IV] is replaced by a cyclohexyl group by reduction.

BEST MODE OF CARRYING OUT THE INVENTION

The invention is further described below by way of examples and reference examples, but the invention is not limited to these examples. In the examples and reference examples, the following abbreviations are used.

NMR: Nuclear magnetic resonance spectrum ($^1$H-NMR)

TLC: Thin layer chromatography

Rf value: Result obtained by using precoated TLC plate silica gel 60F-254 available from Merck (Thickness 0.25 mm).

REFERENCE EXAMPLE 1

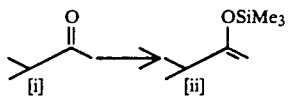

Under nitrogen atmosphere, dry diisopropylamine (116.5 ml, 0.831 mol) was added to dry tetrahydrofurane (300 ml), and stirred. After this solution was cooled to −20° C., n-butyl lithium/hexane solution (1.57M) (529.3 ml, 0.831 mol) was added dropwise, and the resultant mixture was stirred for 30 minutes. Then, this solution was cooled to −70° C. to −65° C., and the solution prepared by dissolving 3-methyl-2-butanone [i] (80.8 ml, 0.755 mol) in dry tetrahydrofurane (300 ml) was added dropwise, followed by stirring for 30-minutes. Afterwards, the reaction mixture was heated up to −10° C. to 0° C. and was cooled down again to −70° C. to −65° C. To this reaction mixture, chlorotrimethyl silane (105.5 ml, 0.831 mol) was added dropwise, and the mixture was stirred overnight. Subsequently, the reaction mixture was concentrated under atmospheric pressure, then diethyl ether (500 ml) and saturated sodium hydrogencarbonate aqueous solution (200 ml) were added to the resultant concentrate. The organic layer was dried over magnesium sulfate anhydride, and the solution was distilled again under atmospheric pressure. In this distillation, fractions having a boiling point of 130° C. or higher were collected, and a colorless and transparent silyl enol ether derivative [ii] (62 g) of 3-methyl-2-butanone was obtained.

EXAMPLE 1

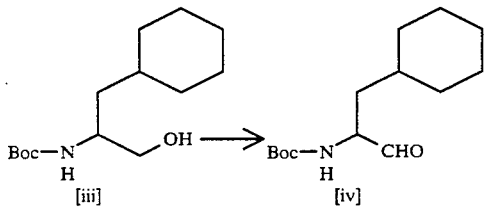

Under nitrogen atmosphere, to (2S)-2-(N-tert-butoxycarbonyl)amino-3-cyclohexyl propanol [iii] (10.0 g, 39 mmol), dry benzene (15 ml) and dry dimethyl sulfoxide (28 ml) were added and stirred to obtain a suspension, and the temperature of the resultant suspension was controlled to 15° C. (internal temperature). Dry triethylamine (27.1 g, 195 mmol) was added to the suspension. While stirring the mixture and keeping the internal temperature thereof from 15 to 25° C., sulfur trioxide/pyridine complex (31.0 g, 195 mmol) was added, and the mixture was directly stirred for an hour, and a brown clear solution was obtained This solution was added into iced water (200 ml) under ice-cooling, and stirred for 5 to 15 minutes. This mixture was transferred into a separating funnel, and extracted with dichloromethane (200 ml×twice). After combining the dichloromethane layers, the resultant organic layer was sequentially washed with saturated sodium hydrogencarbonate aqueous solution (150 ml×twice), 0.5M citric acid aqueous solution (200 ml×4 times), and purified water (200 ml×twice), then dried over magnesium sulfate anhydride. It was sucked and filtered by using a funnel provided with florisil, and a colorless clear solution (about 200 ml) of (2S)-2-(N-tert-butoxycarbonyl)amino-3-cyclohexyl propanal [iv] was obtained.

EXAMPLE 2

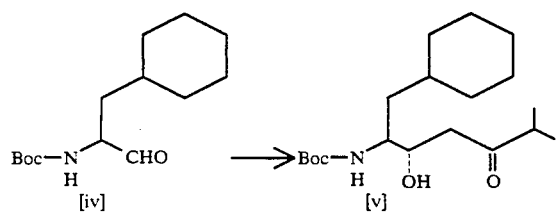

The dichloromethane solution (about 200 ml) of (2S)-2-(N-tert-butoxycarbonyl)amino-3-cyclohexyl propanal [iv] obtained in Example 1 was cooled in dryice/acetone refrigerant, and the liquid temperature was lowered to −78° C. To this solution, the solution prepared by dissolving boron trifluoride diethyl ether complex (5.3 ml, 43 mmol) in dry dichloromethane (50 ml) was added dropwise, and the resultant mixture was stirred for 15 minutes. Furthermore, to this solution, the solution prepared by dissolving the silyl enol ether derivative [ii] (12.3 g, 78 ml) of 3-methyl-2-butanone obtained in Reference Example 1 into dry dichloromethane (50 ml) was added dropwise, and the resultant mixture was stirred for 30 minutes. This reaction solution was added to the mixture of ice (300 g) and sodium hydrogen-carbonate (30 g), and stirred until the ice melts away. This mixture was transferred into a separating funnel, and extracted with diethyl ether (500 ml×once, 200 ml×once). After combining the organic layers, the resultant organic layer was washed with saturated sodium chloride solution (250 ml), and dried over magnesium sulfate anhydride. The dried organic layer was sucked, filtered, and concentrated in vacuo thereby obtaining a mixture containing (5S, 6S)-6-(N-tert-butoxycarbonyl)-amino-7-cyclohexyl-5-hydroxy-2-methyl-3-heptanone [v] and (5R, 6S) stereoisomer with respect to the hydroxyl group thereof in a ratio of about 9:1 (TLC), as a pale yellow oil (9.62 g).

On the other hand, by performing a reaction the same as in Example 2 except for using tin tetrachloride (3.66 ml, 31.24 mmol), a pale yellow oil (4.52 g) was similarly obtained from (2S)-2-(N-tert-butoxycarbonyl)-amino-3-cyclohexyl propanol [iii] (7.3 g, 28.4 mmol). In this case, the ratio of (5S, 6S)-6-(N-tert-butoxycarbonyl)amino-7-cyclohexyl-5-hydroxy-2-methyl-3-heptanone [v] to (5R, 6S) stereoisomer with respect to the hydroxyl group thereof was 8.5:1.5 ($^1$H NMR, TLC). This yellow oil (4.52 g) was separated and refined by silica gel column chromatography, and (5S, 6S)-6-(N-tert-butoxycarbonyl)amino-7-cyclohexyl-5-hydroxy-2-methyl-3-heptanone [v] (2.05 g, 6.0 mmol) was obtained.

$^1$H NMR δ (CDCl$_3$): 4.73 (1 H, br d, J=10 Hz), 4.02 (1 H, m), 3.62 (1 H, m), 3.43 (1 H, s), 2.50–2.70 (3 H, m), 1.45 (9 H, s), 1.00 (6 H, d, J=7 Hz)

TLC: Rf=0.45; (Elution solvent: Ethyl acetate/n-hexane=3/7)

EXAMPLE 3

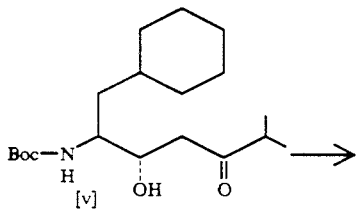

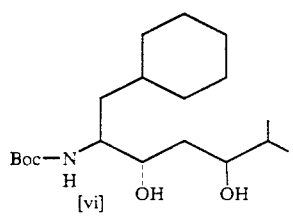

In a 500 ml flask, propionic acid (200 ml) was received and cooled in ice, then tetramethyl ammonium borohydride (10.0 g, 112.7 mmol) was added gradually, and the mixture was stirred for an hour. The pale yellow oil (9.62 g) obtained by using the boron trifluoride diethyl ether complex in Example 2 was dissolved in 50 ml of propionic acid, then the resultant solution was added dropwise to the mixture mentioned above and stirred for 2 hours. Under ice-cooling, the reaction solution was added to a mixture of ice and saturated ammonium chloride aqueous solution, and it was stirred until gas-generation was stopped. It was extracted with chloroform (500 ml×once). The chloroform layer was washed with 2N sodium hydroxide aqueous solution (200 ml×5 times) and saturated brine chloride solution (300 ml×twice), and dried over magnesium sulfate anhydride, then concentrated in vacuo, thereby obtaining a yellowish white solid (9.66 g). This solid matter was heated and dissolved in ethyl acetate (50 ml), then added with hexane (500 ml), and stirring at room temperature for 90 minutes, thereby resulting in crystal precipitation. After sucking and filtering the crystals, they were dried in vacuo, and white crystals of (2S, 3S, 5S)-2-(tert-butoxycarbonyl) amino-1-cyclohexyl-6-methyl-3,5-heptane diol [vi] (3.3 g) were obtained. The amino diol derivative [IV] is a stereoisomer of type (A) described previously, and there are three stereoisomers with respect to the hydroxyl group, that is, of type (B), (C) and (D). In this Example, however, the stereoisomer of type (A) was obtained with very high selectivity so that the stereoisomer [vi] of type (A) was isolated by crystallization only, without purification by silica gel chromatography or the like. The total yield from compound [iii] was 25%.

$^1$H NMR δ (CDCl$_3$): 4.64 (1 H, br d, J=9 Hz), 3.82 (1 H, m), 3.70 (1 H, m), 3.58 (1 H, m), 2.66 (1 H, br d, J=4 Hz), 2.46 (1 H, br d, J=5 Hz), 1.45 (9 H, s), 0.94 (3 H, d, J=7 Hz), 0.90 (3 H, d, J=7 Hz)

[α]$_D$: −52° (c 0.99, MeOH)

Optical purity: 96% e.e.

TLC: Rf=0.48, (Elution solvent: Ethyl acetate/n-hexane=1/1)

EXAMPLE 4

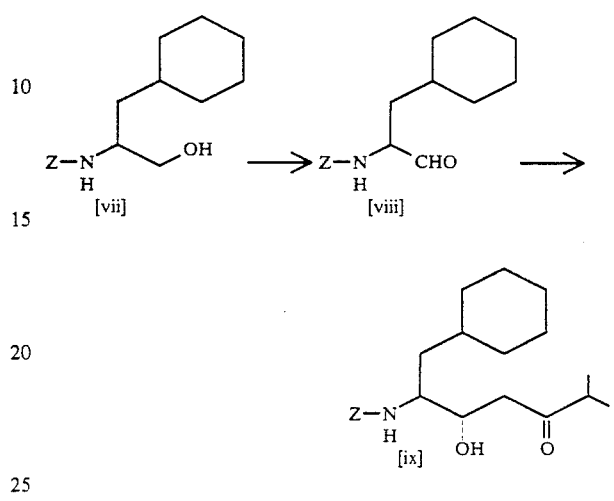

(2S)-2-(N-Benzyloxycarbonyl)amino-3-cyclohexyl propanol [vii] (5.0 g, 17.2 mmol) was oxidized in the same manner as in Example 1, and a dichloromethane solution (500 ml) of (2S)-2-(N-benzyloxycarbonyl-)amino-3-cyclohexyl propanal [viii] was obtained. After cooling 300 ml of this solution to −20° C., the reaction was conducted as in Example 2, by using boron trifluoride diethyl ether complex as the catalyst. As a result, a mixture containing (5S, 6S)-6-(N-benzyloxycarbonyl) amino-7-cyclohexyl-5-hydroxy-2-methyl-3-heptanone [ix] and (5R, 5S) stereoisomer relating to its hydroxyl group at a ratio of about 9:1 (TLC) was obtained as a yellow oil (1.86 g). This yellow oil (1.86 g) was separated and purified by silica gel column chromatogrphy, and (5S, 6S)-6-(N-benzyloxycarbonyl)amino-7-cyclohexyl-5-hydroxy-2-methyl-3-heptanone [ix] (1.03 g, 2.74 mmol) was obtained.

$^1$H NMR δ (CDCl$_3$): 7.25–7.45 (5 H, m), 5.12 (2 H, s), 4.97 (1 H, br d, J=10 Hz), 4.02 (1 H, m), 3.68 (1 H, m), 3.38 (1 H, s), 2.40–2.70 (3 H, m), 1.08 (3 H, d, J=7 Hz), 1.07 (3 H, d, J=7 Hz)

TLC: Rf=0.50, (Elution solvent: Ethyl acetate/n-hexane=3/7)

On the other hand, when the reaction was conducted as in Example 4 using α-amino aldehyde derivative [viii] (0.5 g, 1.73 mmol) purified and isolated by silica gel column chromatography (in this case, racemized), a colorless clear oil (0.635 g) containing the amino hydroxy ketone derivative was obtained. This colorless clear oil (0.1 g) was purified by silica gel thin layer chromatography for preparation (elution solvent: ethyl acetate/n-hexane=2/8), thereby obtaining amino hydroxy ketone derivative [ix] (0.099 g) which was racemized in this case.

EXAMPLE 5

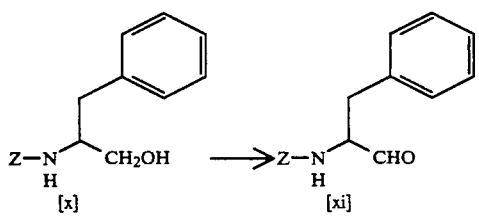

Under nitrogen atmosphere, to (2S)-2-(N-benzyloxycarbonyl) amino-3-phenyl propanol [x] (2.2 g, 7.7 mmol), dry benzene (5 ml) and dimethyl sulfoxide (5 ml) were added and stirred to produce a suspension, which was in turn cooled with ice. Triethylamine (5.4 ml, 38.5 mmol) was added to the solution. While stirring the solution and keeping the internal temperature thereof under 15° C., sulfur trioxide/pyridine complex (6.1 g, 38.5 mmol) was added and stirred for 30 minutes, thereby obtaining a clear brown solution. This solution was added to iced water (50 ml) under ice-cooling, and stirred for 5 to 15 minutes. This mixture was transferred into a separating funnel, and extracted with dichloromethane (80 ml×twice). Combining the dichloromethane layers, the resultant organic layer was washed with 10% citric acid aqueous solution (100 ml×twice), saturated sodium hydrogencarbonate aqueous solution (100 ml×twice), and saturated sodium chloride aqueous solution (100 ml×once), then dried over magnesium sulfate anhydride. Sucking and filtering it, a colorless clear solution of (2S)-2-(N-benzyloxycarbonyl)amino3-phenyl propanal [xi] (about 200 ml) was obtained.

EXAMPLE 6

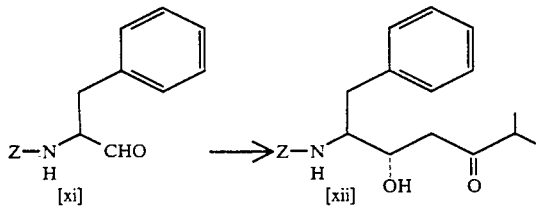

To the dichloromethane solution (about 200 ml) of (2S)-2-(N-benzyloxycarbonyl)amino-3-phenyl propanal [xi] obtained in Example 5, a slight amount of molecular sieve was added. After stirring at room temperature for 30 minutes, the mixture was cooled in dryice/acetone refrigerant to the temperature of −20° C. To this mixture, the solution prepared by dissolving boron trifluoride diethyl ether complex (1.05 ml, 8.48 mmol) in dichloromethane (10 ml) was added dropwise, and the mixture was stirred for 15 minutes. Further to this mixture, the solution containing silyl enol ether derivative [ii] (1.63 g, 10 mmol) of 3-methyl-2-butanone dissolved in dichloromethane (10 ml) was added dropwise, and the mixture was stirred for 30 minutes. This reaction solution was added to saturated sodium hydrogencarbonate aqueous solution (200 ml), and it was stirred until the ice melted away. This mixed solution was transferred into a separating funnel, and extracted with dichloromethane (200 ml). The dichloromethane layer was washed with saturated sodium hydrogencarbonate aqueous solution (300 ml×once) and saturated sodium chloride aqueous solution (300 ml×once), then dried over magnesium sulfate anhydride. By suction filtration and concentration in vacuo, a mixture containing (5S, 6S)-6-(N-benzyloxycarbonyl)amino-5-hydroxy-2-methyl-7-phenyl-3-heptanone [xii] and (5R, 6S) stereoisomer relating to its hydroxyl group at a ratio of 9:1 ($^1$H NMR) was obtained as a pale yellow oil (2.5 g). When the yellow oil was heated and dissolved in ethyl acetate (10 ml), added with hexane (200 ml), and then stirred at room temperature for 10 minutes, crystals were precipitated. By suction filtering of crystals, the stereoisomer was removed as crystals. When the mother liquid was concentrated in vacuo, (5S, 6S)-6-(N-benzyloxycarbonyl)amino-5-hydroxy-2-methyl-7-phenyl-3-heptanone [xii] (2.3 g) was obtained as a pale yellow oil.

$^1$H NMR δ (CDCl$_3$): 7.19–7.37 (10 H, m), 5.19–5.22 (1 H, d), 5.08 (1 H, s), 3.99–4.02 (1 H, d), 3.70–3.80 (1 H, m), 3.53 (1 H, s), 2.50–2.94 (5 H, m), 1.02–1.06 (6 H, m)

TLC: Rf=0.39; (Elution solvent: Ethyl acetate/n-hexane=4/6)

EXAMPLE 7

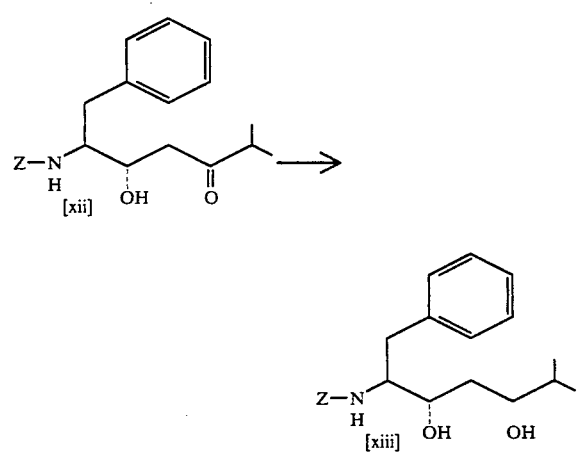

In a 100 ml flask, propionic acid (60 ml) was received and cooled with ice, and tetramethyl ammonium borohydride (1.9 g, 21.7 mmol) was added gradually. Then, the mixture was stirred for an hour while maintaining the ice-cooling. The solution which contains the (5S, 6S)-6-(N-benzyloxycarbonyl)amino-5-hydroxy-2-methyl-7-phenyl-3-heptanone [xii] (2.25 g, 6.09 mmol) obtained in Example 6 was prepared by dissolving the same in propionic acid (20 ml). The solution was added dropwise into the flask under ice-cooling, and the mixture was stirred for 2 hours at room temperature. The reaction solution was added to saturated sodium hydrogencarbonate aqueous solution (100 ml) under ice-cooling, and stirred until gas generation was stopped. The resultant solution was extracted with chloroform (80 ml 3 times). After combining the chloroform layers, the resultant organic layer was washed with 1N sodium hydroxide aqueous solution (100 ml×3 times), saturated sodium hydrogencarbonate aqueous solution (100 ml twice), and saturated sodium chloride aqueous solution (100 ml×once), then dried over magnesium sulfate anhydride, and concentrated in vacuo to obtain a pale yellow solid (2.2 g). The solid was heated and dissolved in ethyl acetate (10 ml), then added with hexane (200 ml), followed by stirring at room temperature for 3 hours to result in crystal precipitation. After the crystals were collected by filtering and dried under vacuum, (2S, 3S, 5S)-2-(N-benzyloxycarbonyl)amino-6-methyl-1-phenyl-3,5-pentane diol [xiii] (1.5 g) was obtained as a white crystal.

$^1$H NMR δ (CDCl$_3$): 7.20–7 40 (10 H, m), 5.07 (3 H, m), 3.90 (2 H, m), 3.56 (1 H, m), 2.90–2.92 (2 H, d), 0.89–0.91 (3 H, d), 0.82–0 85 (3 H, d)

[α]$_D$: −55° (c 1.05, MeOH)

Optical purity: 96% e.e.

TLC: Rf=0.35; (Elution solvent: Ethyl acetate/n-hexane=5/5)

According to the present invention, as described in detail herein, since the α-amino aldehyde derivative [V] obtained by oxidizing the α-amino alcohol derivative represented by formula [VIII] is used in the subsequent reaction (step 2) directly after extraction with dichloromethane, without concentration or purification or isolation, not only racemization of α-amino aldehyde derivative [V] can be prevented, but also the process is extremely simplified. Moreover, since the α-amino aldehyde derivative [V] is reacted with the silyl enol ether derivative represented by formula [IX] by using boron trifluoride ether complex or the like as catalyst, the stereoselectivity (85 to 90% or more) and chemical yield of the objective compound, i.e., amino hydroxy ketone derivative [III], are extremely excellent. Furthermore, since the amino hydroxy ketone derivative [III] is reduced with tetramethyl ammonium borohydride using a lower alkyl carboxylic acid as solvent, the final target compound of amino diol derivative [IV] may be produced stereoselectively (80% or more) and in high chemical yield. Still more, in the present invention, the reaction can proceed consistently from step 1 through step 3 in high yield and stereoselectively, and amino diol derivative [IV] may be easily isolated by crystallization without resort to chromatography or the like.

We claim:

1. A method for stereoselectively preparing the α-amino-β-hydroxy-δ-ketone derivative represented by the following formula,

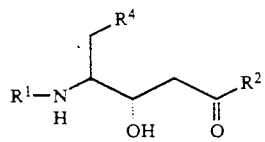

wherein R$^1$ is a protective group for the amino group, R$^2$ is an alkyl group which may be branched, and R$^4$ is a cyclohexyl group or phenyl group, comprising causing the α-amino aldehyde derivative represented by the following formula

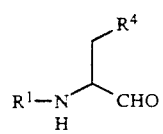

wherein R$^1$ and R$^4$ are the same as above and the silyl enol ether derivative represented by the following formula

wherein R$^2$ is the same as above and R$^3$ is a lower alkyl group which may be branched to react with each other in the presence of boron trifluoride ether complex or tin tetrachloride as catalyst.

2. A method for stereoselectively preparing the α-amino-β-hydroxy-δ-ketone derivative represented by the following formula,

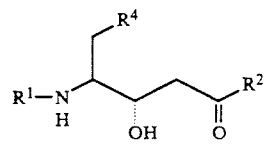

wherein R$^1$, R$^2$ and R$^4$ are the same as in claim 1, comprising oxidizing the α-amino alcohol derivative represented by the following formula in a solvent

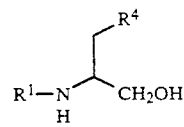

wherein R$^1$ and R$^4$ are the same as in claim 1 to obtain the α-amino aldehyde derivative represented by the following formula,

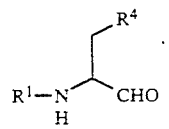

wherein R$^1$ and R$^4$ are the same as in claim 1 and causing said α-amino aldehyde derivative, without isolation, to react directly with the silyl enol ether derivative represented by the following formula in the presence of boron trifluoride ether complex or tin tetrachloride as catalyst

wherein R$^2$ and R$^3$ are the same as in claim 1.

3. A method for stereoselectively preparing the α-amino-β, δ-diol derivative represented by the following formula,

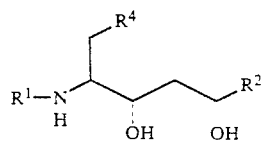

wherein R$^1$, and R$^2$ and R$^4$ are the same as in claim 1, comprising causing the α-amino aldehyde derivative represented by the following formula

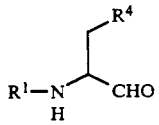

wherein $R^1$ and $R^4$ are the same as in claim 1 and the silyl enol ether derivative represented by the following formula

wherein $R^2$ and $R^3$ are the same as in claim 1 to react with each other in the presence of boron trifluoride ether complex or tin tetrachloride as catalyst, thereby stereoselectively preparing the $\alpha$-amino-$\beta$-hydroxy-$\delta$-ketone derivative represented by the following formula,

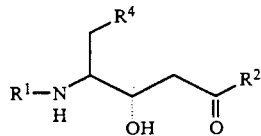

wherein $R^1$, $R^2$ and $R^4$ are the same as in claim 1 and reducing said ketone derivative by using tetramethyl ammonium borohydride in a solvent comprising a lower alkyl carboxylic acid.

4. The method of claim 1, 2, or 3, wherein said protective group $R^1$ is a member selected from the group consisting of a substituted or non-substituted lower alkanoyl group, a lower alkoxycarbonyl group, a substituted or non-substituted aryloxy carbonyl group, a substituted or non-substituted aryl sulfonyl group, and an aralkyl group, said $R^2$ and $R^3$ groups are both a lower alkyl group which can be branched, and said $R^4$ group is a member selected from the group consisting of a cyclohexyl group and a phenyl group.

5. The method of claim 4, wherein said substituted or non-substituted lower alkanoyl group is a member selected from the group consisting of a formyl group, an acetyl group, a propionyl group, and a trifluoroacetyl group, said lower alkoxycarbonyl group is a member selected from the group consisting of a tert-butoxy carbonyl group and a tert-amyloxy carbonyl group; said substituted or non-substituted aryloxy carbonyl group is a member selected from the group consisting of a benzyloxy carbonyl group and a p-nitrobenzyloxy carbonyl group; said substituted or non-substituted aryl sulfonyl group is a tosyl group; said aralkyl group is a member selected from the group consisting of a trityl; group and a benzyl group; and said lower alkyl group $R^2$ or $R^3$ which can be branched is a member selected from the group consisting of a methyl group, an ethyl group, an n-propyl group, an isopropyl group, an n-butyl group, an isobutyl group, a sec-butyl group, a tert-butyl group, an n-pentyl group, a 1-methyl butyl group, a 2,2-dimethyl butyl group, an n-hexyl group, a 2-methylpentyl group, and a 2,2-dimethylpropyl group.

6. The method of claim 5, wherein said lower alkyl group $R^3$ is a member selected from the group consisting of a methyl group, an ethyl group, a propyl group, an isopropyl group, an n-butyl group, an isobutyl group, a sec-butyl group, and a tert-butyl group.

7. The method of claim 1, wherein said catalyst is boron trifluoride ether complex.

8. The method of claim 7, further comprising using a non-protonic solvent.

9. The method of claim 8, wherein said non-protonic solvent is a member selected from the group consisting of dichloromethane, chloroform, carbon tetrachloride, and toluene.

10. The method of claim 1, wherein the reaction temperature is $-80°$ to $0°$ C.

11. The method of claim 1, wherein the ether in said ether complex is a member selected from the group consisting of diethyl ether and di-n-butyl ether.

12. The method of claim 3, wherein said lower alkyl carboxylic acid is propionic acid.

13. The method of claim 3, wherein the reaction temperature is $-10°$ to $0°$ C.

* * * * *